(12) United States Patent
Bille et al.

(10) Patent No.: US 6,730,074 B2
(45) Date of Patent: May 4, 2004

(54) CORNEA CONTACT SYSTEM FOR LASER SURGERY

(75) Inventors: Josef Bille, Heidelberg (DE); Klaus Baumeister, Sinsheim-Adersbach (DE); Frieder Loesel, Mannheim (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 25 days.

(21) Appl. No.: 10/155,810

(22) Filed: May 24, 2002

(65) Prior Publication Data

US 2003/0220629 A1 Nov. 27, 2003

(51) Int. Cl.$^7$ .................................................. A61F 9/01
(52) U.S. Cl. .............................. 606/5; 606/4; 128/898
(58) Field of Search ........................ 606/4, 5; 128/898

(56) References Cited

U.S. PATENT DOCUMENTS

| | | | |
|---|---|---|---|
| 4,391,275 A | | 7/1983 | Fankhauser |
| 4,772,115 A | | 9/1988 | Gersten |
| 5,049,147 A | * | 9/1991 | Danon ........................... 606/4 |
| 5,098,426 A | * | 3/1992 | Sklar et al. ..................... 606/4 |
| 5,108,412 A | | 4/1992 | Krumeich |
| 5,226,903 A | * | 7/1993 | Mizuno ......................... 606/4 |
| 5,336,215 A | * | 8/1994 | Hsueh et al. ................... 606/4 |
| 5,647,865 A | * | 7/1997 | Swinger ........................ 606/5 |
| 5,984,916 A | | 11/1999 | Lai |
| 6,099,522 A | | 8/2000 | Knopp et al. |
| 6,224,211 B1 | * | 5/2001 | Gordon .......................... 606/5 |
| 6,271,914 B1 | | 8/2001 | Frey |
| 6,271,915 B1 | | 8/2001 | Frey |
| 6,325,792 B1 | * | 12/2001 | Swinger et al. ................. 606/4 |
| 6,451,006 B1 | * | 9/2002 | Bille ............................. 606/5 |
| 6,540,353 B1 | * | 4/2003 | Dunn ............................ 606/5 |
| 2003/0014042 A1 | * | 1/2003 | Juhasz et al. ................... 606/5 |
| 2003/0100893 A1 | * | 5/2003 | Bille ............................. 606/4 |

FOREIGN PATENT DOCUMENTS

| WO | WO 94/09849 | 5/1994 |
|---|---|---|
| WO | WO 02/085247 A2 | 10/2002 |

OTHER PUBLICATIONS

J. Bahr, Realization of Refractive Continuous Phase Elements with High Design Freedom by Mask Structured Ion Exchange.

* cited by examiner

Primary Examiner—Roy D. Gibson
Assistant Examiner—Henry M. Johnson
(74) Attorney, Agent, or Firm—Nydegger & Associates

(57) ABSTRACT

A system for accurately guiding a laser focal point along a predetermined path within the stroma of a cornea includes a contact lens for conforming the anterior surface of the cornea to a radius of curvature, $R_{lens}$, that is approximately 8.3 mm. Conforming the cornea to the lens causes minimal discomfort to the patient and does not upset the three-dimensional architecture of the corneal lamellae. As the focal point is advanced along a path within the cornea, the laser source is selectively translated parallel to the optical axis of the cornea to control the depth of the laser focal point. The movement includes three components: a first component, $z_1$ that is dependent upon the shape of the contact lens, a second component, $z_2$ that compensates for refraction at the surfaces of the contact lens, and a third component, $z_3$, that compensates for refraction caused by the anatomical configuration of the cornea.

16 Claims, 2 Drawing Sheets

CORNEA CONTACT SYSTEM FOR LASER SURGERY

FIELD OF THE INVENTION

The present invention pertains generally to ophthalmic laser surgery systems and procedures. More particularly, the present invention pertains to a contact lens for use in conjunction with a surgical procedure that allows a surgical laser to be precisely focused at a predetermined location within the cornea of a patient's eye. The present invention is particularly, but not exclusively, useful for creating a corneal flap that can be subsequently used in a surgical procedure to improve a patient's vision by altering the shape of the patient's cornea.

BACKGROUND OF THE INVENTION

There are many surgical procedures in which it is desirable to be able to focus a laser beam at a predetermined location within a patient's cornea with precision and accuracy. One such surgical procedure involves the creation of a corneal flap that can be lifted to expose stromal tissue. Once exposed, the stromal tissue can be vaporized using a laser to reshape the cornea. An example of a procedure that uses a laser beam focused at a predetermined location within a patient's cornea is disclosed in U.S. Pat. No. 4,907,586, which issued to Bille et al. for an invention entitled "Method for Reshaping the Eye". In greater detail, the above-cited Bille patent discloses the use of a pulsed laser beam for subsurface photoablation of intrastromal tissue. Unlike the excimer laser, the pulsed laser beam, as disclosed by Bille, penetrates corneal tissue and can be focused at a point below the surface of the cornea to photoablate stromal tissue at the focal point. The ability to reach a subsurface location without necessarily providing a physical pathway allows for volumes of stromal tissue having complex shapes to be accurately photoablated, while minimizing the amount of total tissue disrupted.

When considering subsurface photoablation, a general knowledge of the anatomy of the cornea is helpful. In detail, the human cornea comprises various layers of tissue that are structurally distinct. In order, going in a posterior direction from outside the eye toward the inside of the eye, the various layers in a cornea are: an epithelial layer, Bowman's membrane, the stroma, Decemet's membrane, and an endothelial layer. Of these various structures, the stroma is the most extensive and is generally around four hundred microns thick. It happens that the healing response of the stromal tissue is generally quicker than the other corneal layers. Because of the relative abundance of stromal tissue and its healing response, stromal tissue is generally selected for removal in refractive correction procedures.

In detail, the stroma of the eye is comprised of around two hundred identifiable and distinguishable layers of lamellae. Each of these layers of lamellae in the stroma is generally dome-shaped, like the cornea itself, and they each extend across a circular area having a diameter of approximately nine millimeters. Unlike the layer that a particular lamella is in, each lamella in the layer extends through a shorter distance of only about one tenth of a millimeter (0.1 mm) to one and one half millimeters (1.5 mm). Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, each individual lamella is only about two microns thick.

Another important characteristic of the stroma is the strength of the stromal tissue. In greater detail, the strength of the tissue within a lamella is approximately fifty times the strength that is provided by the adhesive tissue that holds the layers of lamellae together. Thus, much less laser energy is required to separate one layer of a lamella from another layer (i.e. peel them apart), than would be required to cut through a lamella. Along these lines, co-pending U.S. patent application Ser. No. 09/783,665, filed on Feb. 14, 2001 by Bille and entitled "A Method for Separating Lamellae" discloses a method for finding an interface between layers of lamellae for efficient photoablation. As disclosed in co-pending application Ser. No. 09/783,665 (hereinafter Bille '665), a wavefront analyzer in conjunction with an ellipsometer can be used to maintain the focal point of a laser beam on an interface between layers of lamellae during creation of a corneal flap for a LASIK type procedure. Use of this technique to photoablate the entire inner surface for a flap has been disclosed in Bille '665.

A somewhat similar method for creating a LASIK type flap is disclosed in co-pending U.S. patent application Ser. No. 09/997,167, filed on Nov. 28, 2001 by Bille and entitled "A Method for Creating a Corneal Flap". As disclosed in co-pending application Ser. No. 09/997,167, a periphery for a flap can be created using subsurface photoablation along an interface between layers of lamellae. The periphery, in turn, can be used as a starting point to allow layers of lamellae to be mechanically separated from each other along an interface by simply grasping and peeling the flap away from the remainder of the cornea.

In either of these methods wherein photoablation along an interface is desired, the overall movement of the laser focal point is generally along a curved path that is at a substantially constant depth from the anterior surface of the cornea. Thus, it is generally necessary to provide a system to move the laser focal point along this curved path. As the focal point is moving along the generally curved path, a wavefront analyzer and an ellipsometer can be used periodically to verify that photoablation is occurring on an interface between layers of lamellae. When a photoablation response indicates that photoablation is no longer occurring on an interface, a minor adjustment can be made to the depth of the laser focal point to resume photoablation on the interface.

With this in mind, the present invention is focused primarily on providing systems and methods for moving the laser focal point along the curved path (i.e. along paths that are generally parallel to the anterior surface of the cornea). On the other hand, co-pending applications Ser. Nos. 09/783,665 and 09/997,167 provide systems and methods for making minor adjustments to the depth of the laser focal point to maintain the laser focal point on the interface between layers of lamellae. As such, the contents of co-pending application Ser. Nos. 09/783,665 and 09/997,167 are hereby incorporated herein by reference. It follows from the above discussion that the systems and methods for moving the laser focal point along the curved path must be extremely accurate (i.e. accuracy on the order of ±2 μm) if these systems are to be used to maintain a laser focal point on an interface between layers of lamellae.

Another factor that must be considered when creating corneal flaps by subsurface stromal photoablation is the elastic compressibility of the lamellae in the cornea. Specifically, it is known that the elastic compressibility of the lamellae varies within the cornea with the elastic compressibility being greatest near the center of the cornea. The consequence of this variation in elastic compressibility becomes significant if the cornea is flattened excessively during subsurface stromal photoablation. During severe flattening of the cornea, the three-dimensional architecture of the lamellae in the cornea becomes distorted. The result of this distortion is that an incision that is made while the cornea is severely flattened changes shape in an unpredictable way when the cornea is relaxed.

Still another factor that must be considered when creating corneal flaps by subsurface stromal photoablation is the beam path of the laser beam. Ideally, all beam paths used to create the flap would be oriented normal to the anterior surface of the cornea to eliminate complications due to refraction of the laser beam at the anterior surface. Unfortunately, typical laser delivery systems are not agile enough to maintain the laser beam on beam paths that are oriented normal to the anterior surface. Thus, for procedures where high precision is required, some compensation must be made for these deviations in beam path due to refraction. Additionally, the optical properties of the cornea, such as corneal density and birefringence, vary from location to location within the cornea. These optical properties can also alter the beam path of a surgical laser beam, and accordingly, it is also desirable to compensate for these deviations in beam path.

In light of the above, it is an object of the present invention to provide systems and methods for creating a corneal flap suitable for use in a corneal reshaping procedure. Another object of the present invention is to provide systems and methods for accurately guiding a laser focal point along a predetermined curved path within the cornea such as an interface between layers of lamellae. It is yet another object of the present invention to provide a contact lens for use in a subsurface stromal photoablation procedure that stabilizes the cornea without upsetting the three-dimensional architecture of the corneal lamellae. It is still another object of the present invention to provide a contact lens for use in a subsurface stromal photoablation procedure that imparts a known radius of curvature to the anterior surface of the cornea to thereby allow a laser focal point to be guided along a path within the cornea relative to the anterior surface of the cornea. Another object of the present invention is to provide systems and methods for accurately guiding a laser focal point along a predetermined path within the cornea that compensate for beam refraction by selectively moving the laser source in a direction parallel to the optical axis of the eye. It is yet another object of the present invention to provide systems and methods for accurately guiding a laser focal point along a predetermined path within the cornea that compensate for variations in the optical properties of the cornea by selectively moving the laser source in a direction parallel to the optical axis of the eye. It is still another object of the present invention to provide a contact lens having a refractive index gradient that compensates for variations in the optical properties of the cornea to thereby allow a laser focal point to be accurately guided along a predetermined path within the cornea. Still another object of the present invention is to provide a contact lens having a refractive index gradient that compensates for beam refraction to thereby allow a laser focal point to be accurately guided along a predetermined path within the cornea. Still another object of the present invention is to provide systems and methods for creating corneal flaps that are easy to use and comparatively cost effective.

SUMMARY OF THE PREFERRED EMBODIMENTS

The present invention is directed to a system and method for accurately guiding a laser focal point along a predetermined path within the stroma of the cornea. For the present invention, the system includes a contact lens for conforming the anterior surface of a patient's cornea to a known radius of curvature. In detail, the contact lens has a posterior surface and an anterior surface. Preferably, the contact lens has a substantially constant thickness with the anterior surface being spaced from the posterior surface by a distance of approximately 0.2 mm. Importantly, the posterior surface of the contact lens has a substantially uniform radius of curvature, $R_{lens}$, that is approximately 8.3 mm.

For the present invention, the contact lens is preferably made of a clear material, such as plastic to thereby allow a surgical laser beam to be passed through the contact lens. In a first embodiment of the present invention, the contact lens has a substantially uniform index of refraction that closely matches the index of refraction of a typical cornea to minimize refraction at the interface between the contact lens and the cornea. An exemplary contact lens for this first embodiment is prepared having a uniform index of refraction of approximately 1.4 (as compared to a typical index of refraction for the human cornea which is approximately 1.37).

In accordance with the present invention, the contact lens in mounted in a suction ring. In use, the posterior surface of the contact lens is gently pressed again the anterior surface of the cornea until the anterior surface of the cornea conforms to the posterior surface of the contact lens. Next, scleral suction is applied via the suction ring to hold the contact lens against the cornea. Because the anterior surface of a typical cornea has a radius of curvature that is approximately 7.8 mm, the anterior surface of the cornea will conform to the posterior surface of the contact lens ($R_{lens}$= 8.3 mm) when the posterior surface of the contact lens is pressed against the cornea. If desired, the suction ring can be attached to a fixed structure, such as the laser source base, to stabilize the eye during the laser procedure. Importantly, this slight flattening of the cornea causes minimal discomfort to the patient and does not upset the three-dimensional architecture of the corneal lamellae.

In accordance with the present invention, a laser source is provided to generate a surgical laser beam. Included in the laser source is a cutting lens to focus the laser beam to a subsurface focal point within the cornea for the purpose of photoablating stromal tissue. The laser source is positioned relative to the patient's eye to allow a laser beam to be generated and directed along a first beam path that is collinear with the optical axis of the eye (hereinafter referred to as the z-axis). It is to be appreciated that this first beam path is substantially normal to the anterior surface of the contact lens at the incident point where the first beam path passes through the anterior surface of the contact lens.

For the present invention, the laser source is mounted on a scanning mechanism to allow the focal point of the laser beam to be scanned along a predetermined path within the cornea. In greater detail, the scanning mechanism is capable of moving the laser source within a plane that is normal to the optical axis. As the laser source moves within the plane, the laser beam is placed on successive beam paths, with each beam path passing through a different incident point on the anterior surface of the contact lens.

Because the anterior surface of the contact lens is curved, each point on the surface defines a unique surface normal. With the cooperation of structure described above, each off-axis beam path passes through the anterior surface of the contact lens at an angle to the surface normal that is defined at the point of incidence. Because of this angle, a laser beam traveling on an off-axis beam path will be refracted at the anterior surface of the contact lens. However, the scanning mechanism does provide some additional tilting of the laser beam when the laser source is positioned at a distance from the z-axis. More specifically, as the laser source is moved radially away from the z-axis, the tilt of the laser beam relative to the z-axis increases. Typically, this tilting occurs at a rate of approximately 1/mm of radial distance that the laser source is moved from the optical axis. More specifically, at the outer periphery of the cornea, the laser beam has moved radially about 4 mm from the z-axis and has tilted through an angle of approximately 3° from the z-axis.

In accordance with the present invention, the scanning mechanism can also selectively move the laser source in a direction parallel to the z-axis. It is to be appreciated that movements of the laser source in a direction parallel to the z-axis will result in corresponding movements of the focal point of the laser beam in a direction parallel to the z-axis. As the focal point moves along a curved path within the cornea, the z-axis movement of the focal point allows the system to control the depth of the focal point (measured from the anterior surface of the cornea). The magnitude, z, of the z-axis movement required to control the depth of the focal point as the focal point moves along a curved path includes three components; $z_1$, $z_2$ and $z_3$. The first component, $z_1$, is geometrical and does not include the effects of refraction. This first component, $z_1$ is dependent upon the shape of the contact lens and any contribution due to the tilt of the laser beam relative to the optical axis. The second component, $z_2$, compensates for refraction that occurs at the surfaces of the contact lens. The third component, $z_3$, compensates for refraction caused by the anatomical configuration of the cornea.

For example, consider the case where photoablation along an interface between two lamellae is desired. With the anterior surface of the cornea conforming to the contact lens ($R_{lens}$=8.3 mm), it is to be expected that an interface between lamellae will also lie along a curved path having a radius of curvature of about 8.3 mm. Thus, a $z_1$ movement of the laser focal point is required to maintain the focal point on the interface between lamellae layers during movement of the focal point along the interface. Specifically, to maintain the focal point at a constant depth from the anterior surface of the cornea (i.e. depth into the cornea), a $z_1$ movement of approximately 1.5 mm must be made as the focal point moves from a point on the z-axis to a point approximately 4 mm from the z-axis near the periphery of the cornea.

In addition to the $z_1$ movements required to follow the radius of curvature of the lens with the focal point, $z_2$ movements can be used to compensate for the effects on focal point depth from refraction that occurs at the surfaces of the contact lens. The magnitude of the $z_2$ correction varies in magnitude from zero on the optical axis to about 7 $\mu$m at a point approximately 4 mm from the z-axis near the periphery of the cornea.

As indicated above, the third component, $z_3$, compensates for refraction caused by the anatomical configuration of the cornea. Specifically, it is known that the density and birefringent properties of the cornea vary from location to location within the cornea. As the focal point moves along a path within the cornea, variations in the density and birefringent properties of the cornea will effect the depth of the focal point. These variations in the density and birefringent properties of the cornea, however, can be compensated by $z_3$, movements. More specifically, the density of the cornea can be measured and mapped using wavefront analysis and the birefringent properties of the cornea can be measured and mapped using an ellipsometer. The maps can then be used to calculate $z_3$ movements that will compensate for these variations in corneal properties. Typical values for a $z_3$ correction will be in the range of 5–8 $\mu$m.

In another embodiment of the present invention, a contact lens having a non-uniform index of refraction is used to compensate for effects on focal point depth from refraction that occurs at the surfaces of the contact lens and variations in corneal properties. Thus, for this embodiment, the $z_2$ and $z_3$ movements of the laser source can be reduced or eliminated. For the present invention, the non-uniform index of refraction can be accomplished by ion implantation of the plastic lens using masking techniques. To compensate for effects on focal point depth from refraction that occurs at the surfaces of the contact lens, a contact lens having an index of refraction profile is used. Since this refraction is characteristic of the lens shape, the index of refraction profile will be the same for all lenses having the same shape. Specifically, for this embodiment, the portion of the contact lens that is on the z-axis will have the highest index of refraction while the periphery of the contact lens will have an index of refraction that is reduced by about 3 percent.

To compensate for effects on focal point depth due to the anatomical configuration of the cornea, a corneal mapping of the density and birefringent properties of the cornea is first prepared as described above. With the mapping, a contact lens can be selectively altered via ion implantation to compensate for the variations in corneal properties. Thus, the required contact lens will differ from patient to patient. However, it is contemplated that all corneas can be classified into about twenty anatomically similar groups. Thus only about twenty different contact lenses are required to compensate for the anatomical configuration of the cornea with reasonable accuracy.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
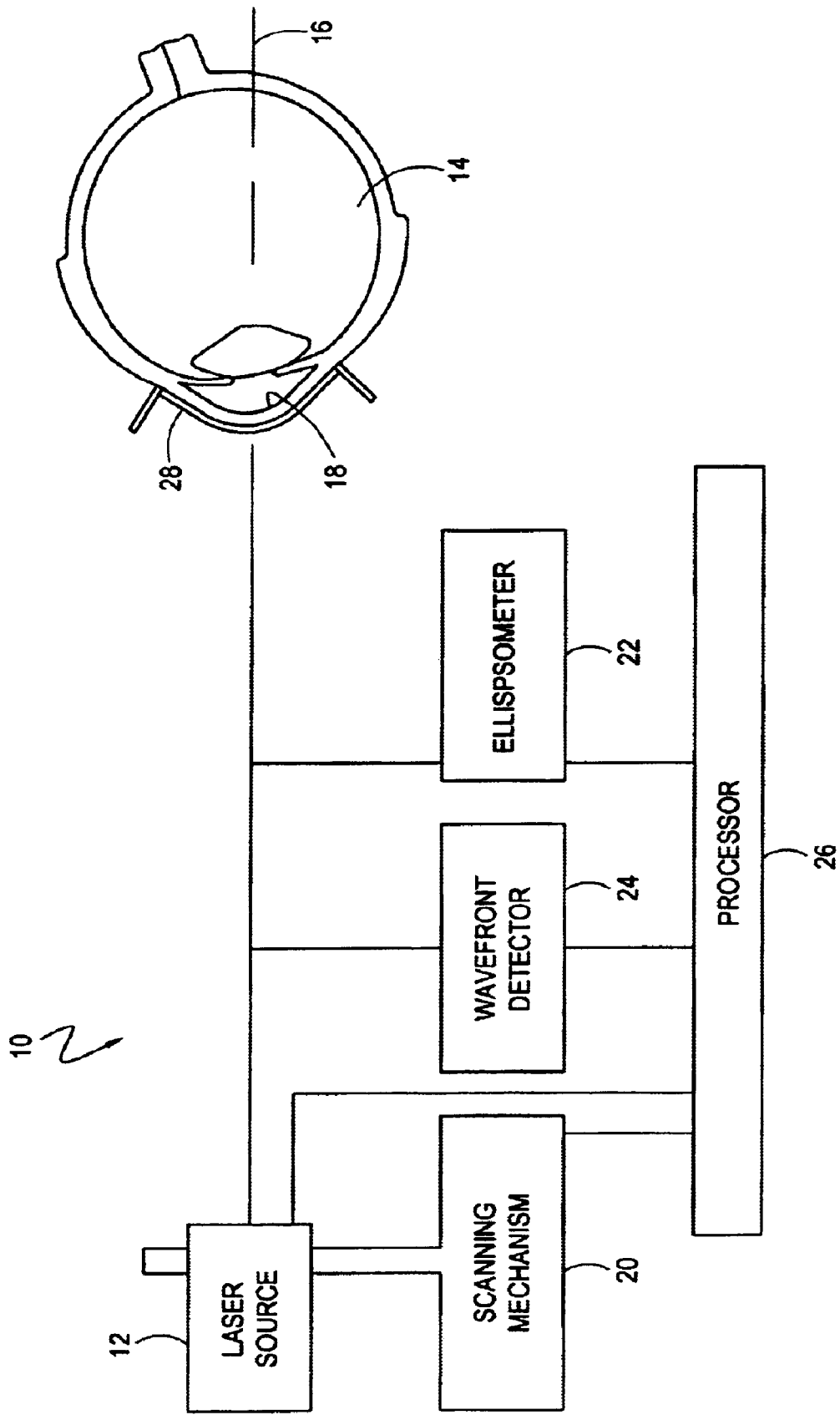
FIG. 1 is a simplified, schematic diagram showing the operative components of a system in accordance with the present invention.

Referring initially to FIG. 1, a system in accordance with the present invention is shown schematically and generally designated 10. As shown, the system 10 includes a laser source 12 to generate a laser beam. As shown, the laser source 12 is positioned relative to the eye 14 to allow a laser beam to be directed along a beam path that is collinear with the optical axis 16 of the eye 14. Additionally, the laser source 12 includes a cutting lens to focus the laser beam to a focal point within the cornea 18 of the eye 14. Although an application of the present invention wherein a laser focal point is moved within the cornea 18 is described herein, those skilled in the art will appreciate that the present invention can be used in other applications where it is desirable to move a laser focal point within a resilient transparent material. In a particular application of the present invention wherein it is desired to use the laser beam to photoablate stromal tissue, the laser source 12 preferably has a photoablation mode in which the laser source 12 generates a continuous train of ultra-short pulses, with each pulse having a pulse duration of approximately one picosecond. Specifically, it is necessary that each pulse have an energy level that is above the threshold necessary for the photoablation of stromal tissue (i.e. above approximately one and one half microjoules per ten micron diameter spot size).

Continuing now with reference to FIG. 1, it can be seen that the system 10 further includes a scanning mechanism 20 for moving the laser source 12 relative to the eye 14. As detailed further below, as the laser source 12 is moved by the scanning mechanism 20, the laser beam is placed on successive beam paths into the cornea 18 to allow the focal point of the laser beam to be moved along a predetermined path. As further shown in FIG. 1, the system 10 can also include an ellipsometer 22 that is capable of determining the birefringent properties within stromal tissue. For the purposes of the present invention, a suitable type of ellipsometer is disclosed and claimed in U.S. Pat. No. 5,822,035, which issued to Bille for an invention entitled "Ellipsometer." Further, FIG. 1 shows that the system 10 can include a wavefront detector 24, such as a Hartmann-Shack sensor, which is capable of modeling a wavefront. Additionally, as shown, the system 10 includes a processor 26 which is preferably a dedicated computer. The processor 26 is provided to process data and control the other components of the system 10 including the scanning mechanism 20. FIG. 1 also shows that the system 10 includes a contact lens 28 for conforming the cornea 18 and stabilizing the eye 14 during the laser procedure. As detailed more fully below, these components of the system 10 cooperate in combination to accurately guide a laser focal point along a predetermined path within the cornea 18.

Figure 2:
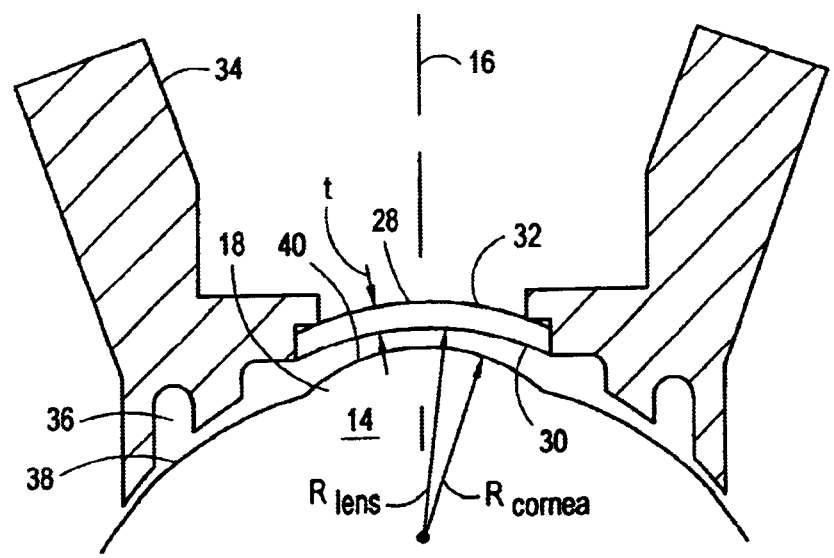
FIG. 2 is an enlarged, sectional view of the cornea and a contact lens suitable for use in the present invention with the contact lens shown immediately prior to engagement with the cornea.

A better appreciation of the contact lens 28 can be obtained with reference to FIG. 2. As shown, the contact lens 28 has a posterior surface 30 and an anterior surface 32. Preferably, the contact lens 28 has a substantially constant thickness, t, with the anterior surface 32 being spaced from the posterior surface 30 by a thickness, t, of approximately 0.2 mm. Importantly, the posterior surface 30 of the contact lens 28 has a substantially uniform radius of curvature, $R_{lens}$, that is approximately 8.3 mm. Importantly, the contact lens 28 is made of a material that is transparent to the laser beam to thereby allow the laser beam to pass through the contact lens 28. In a first embodiment of the present invention, the contact lens 28 is made of a plastic that has a substantially uniform index of refraction, $\eta_{lens}$, that closely matches the index of refraction of a typical cornea, $\eta_{cornea}$, to minimize refraction at the interface between the contact lens 28 and the cornea 18. An exemplary contact lens for this first embodiment is prepared having a uniform index of refraction, $\eta_{lens}$ of approximately 1.4 (as compared to a typical index of refraction for the human cornea, $\eta_{cornea}$ which is approximately 1.37).

With continued reference to FIG. 2, it can be seen that the contact lens 28 is preferably mounted in a suction ring 34. As shown, the suction ring 34 surrounds the contact lens 28 and includes one or more suction ports 36 that are positioned to hold the suction ring 34 against the sclera 38 of the eye 14. In use, the posterior surface 30 of the contact lens 28 is gently pressed against the anterior surface 40 of the patient's cornea 18 until the anterior surface 40 of the cornea 18 conforms to the posterior surface 30 of the contact lens 28. Thus, the contact lens 28 is used to conform the anterior surface 40 of the cornea 18 to a known radius of curvature. Next, scleral suction is applied via the suction ring 34 to hold the contact lens 28 against the cornea 18. Because the anterior surface 40 of a typical cornea 18 has a radius of curvature, $R_{cornea}$, that is approximately 7.8 mm, the anterior surface 40 of the cornea 18 will conform to the posterior surface 30 of the contact lens 28 ($R_{lens}$=8.3 mm) when the posterior surface 30 is pressed against the cornea 18. If desired, the suction ring 34 can be attached to a fixed structure (attachment not shown) to stabilize the eye 14 during the laser procedure. Importantly, when the cornea 18 is conformed to the contact lens 28, only minimal discomfort to the patient results and the three-dimensional architecture of the corneal lamellae is not upset.

Figure 3:
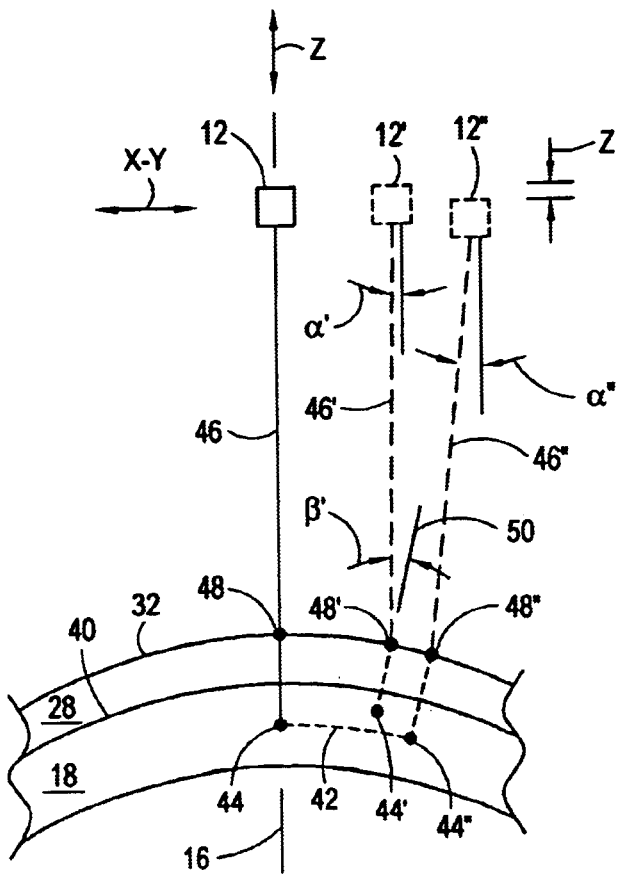
FIG. 3 is a simplified schematic view of a laser source and a portion of a cornea and contact lens showing the effect of various movements of the laser source on the laser focal point.

Use of the system 10 to accurately guide a laser focal point along a predetermined path 42 within the cornea 18 can best be appreciated with cross reference to FIGS. 1 and 3. For illustration purposes, consider an exemplary predetermined path 42 as shown in FIG. 3. As shown, the predetermined path 42 begins at a point on the optical axis 16 and extends within the cornea 18 at a substantially constant depth from the anterior surface 40 of the cornea 18. Such a predetermined path 42 may be part of surgical incision necessary to create the interior surface of LASIK type flap. Also, it is to be appreciated that the predetermined path 42 may represent a path along an interface between layers of lamellae, with the interface being at a substantially constant depth from the anterior surface 40 of the cornea 18. Although the exemplary predetermined path 42 as shown is useful for illustration of the present invention, it is to be appreciated that the present invention is applicable to other predetermined paths within the cornea 18 to include predetermined paths that are not at a substantially constant depth from the anterior surface 40 of the cornea 18, predetermined paths that do not pass through the optical axis 16 and predetermined paths that do not lie entirely within the stroma portion of the cornea 18.

With continued cross-reference to FIGS. 1 and 3, it can be seen that the laser source 12 can be moved relative to the cornea 18 to move the focal point 44 along the predetermined path 42. Specifically, a scanning mechanism 20 is used to move the laser source 12, with the scanning mechanism 20 having the ability to move the laser source 12 within an X-Y plane that is normal to the optical axis 16. Additionally, the scanning mechanism 20 is able to move the laser source 12 in directions that are parallel to the optical axis 16 (i.e. in the Z direction). The scanning mechanism 20, in turn, performs these movements in response to instructions from the processor 26. Inputs to the processor 26 can include the coordinates of the predetermined path 42, the geometry and index of refraction of the contact lens 28, as well as other inputs described below.

FIG. 3 shows the laser source 12 initially oriented to direct a laser beam along a beam path 46 that is collinear to the optical axis 16. As shown, the laser beam passes through the anterior surface 32 of the contact lens 28 at an incident point 48 and continues on to a focal point 44 on the predetermined path 42. As shown, the beam path 46 is substantially normal to the anterior surface 32 at the incident point 48, and accordingly there is no refraction of the laser beam at the anterior surface 32.

FIG. 3 further shows the position of the laser source (labeled 12'), after translation of the laser source 12 within the X-Y plane. As shown, a laser beam from the laser source 12' follows a beam path 46' that passes through the anterior surface 32 of the contact lens 28 at an incident point 48' and continues on to a focal point 44' that is not on the predetermined path 42. A surface normal 50 that is orthogonal to the anterior surface 32 of the contact lens 28 at the incident point 48' is shown. As shown, the beam path 46' passes through the anterior surface 32 at an angle, β', to the surface normal 50. Because of this angle, β', a laser beam traveling on beam path 46' is refracted at the anterior surface 32 of the contact lens 28. As shown, this refraction affects the depth of the focal point 44', causing the laser beam to focus before reaching the predetermined path 42. However, as shown, the scanning mechanism 20 tilts the laser beam at an angle α' relative to the optical axis 16 when the laser source 12' is positioned at a distance from the optical axis 16. More specifically, it can be seen in FIG. 3 that as the laser source 12 is moved radially away from the optical axis 16, the tilt of the laser beam relative to the optical axis 16 increases. Typically, this tilting occurs at a rate of approximately 1°/mm of radial distance that the laser source 12 is moved from the optical axis 16. More specifically, at the outer periphery of the cornea 18, the laser beam has moved radially about 4 mm from the optical axis 16 and has tilted through an angle, α, of approximately 3° from the optical axis 16. Although this slight tilting of the laser beam reduces refraction of the laser beam at the anterior surface 32 of the contact lens 28, significant refraction at the anterior surface 32 of the contact lens 28 remains.

In addition to the effects of refraction, there are several other reasons why the laser beam emanating from the laser source 12' focuses before reaching the predetermined path 42. First, as shown, the predetermined path 42 is curved in the Z direction away from the X-Y plane, following the curvature of the anterior surface 40 of the cornea 18. On the other hand, the laser source 12' remains positioned in the original X-Y plane. Additionally, the tilt of the laser beam relative to the optical axis 16 decreases the depth of the focal point 44'. Thus, as the tilt of the laser beam relative to the optical axis 16 becomes larger, the depth of the focal point 44' from the anterior surface 40 becomes smaller. Also, refraction caused by the anatomical configuration of the cornea 18 can affect the depth of the focal point 44'. Specifically, it is known that the density and birefringent properties of the cornea 18 vary from location to location within the cornea 18. As the laser beam moves within the cornea 18, variations in the density and birefringent properties of the cornea 18 will effect the depth of the focal point 44'.

Importantly for the present invention, the scanning mechanism 20 can selectively move the laser source 12 in a direction parallel to the optical axis 16 to compensate for the effects from the curvature of the predetermined path 42, refraction due to the contact lens 28, tilt of the laser beam and refraction caused by the anatomical configuration of the cornea 18. FIG. 3 shows the position of the laser source (labeled 12"), after translation of the laser source 12 within the X-Y plane and translation of the laser source 12 through a distance, z, parallel to the optical axis 16. As shown, a laser beam from the laser source 12" follows a beam path 46" that passes through the anterior surface 32 of the contact lens 28 at an incident point 48" and continues on to a focal point 44" that is on the predetermined path 42.

It follows from the above discussion that the magnitude, z, of the movement of the laser source 12" in the Z direction to place the focal point 44" on the predetermined path 42 can include three components; $z_1$, $z_2$ and $z_3$. The first component, $z_1$, is geometrical and does not include the effects of refraction. This first component, $z_1$ is dependent upon the shape of the predetermined path 42 (which is generally affected by the shape of the contact lens 28) and the tilt of the laser beam relative to the optical axis 16. To maintain the focal point 44 at a constant depth from the anterior surface 40 of the cornea 18, a $z_1$ movement of approximately 1.5 mm must be made as the focal point 44 moves from a point on the optical axis 16 to a point approximately 4 mm from the optical axis 16 near the periphery of the cornea 18. Inputs to the processor 26 to calculate the $z_1$ correction can include the coordinates of the predetermined path 42, the geometry of the contact lens 28 and the tilt of the laser beam relative to the optical axis 16.

The second component, $z_2$, compensates for refraction that occurs at the surfaces of the contact lens 28. Typically, the magnitude of the $z_2$ correction will vary in magnitude from zero on the optical axis 16 to about 7 μm at a location approximately 4 mm from the optical axis 16 near the periphery of the cornea 18. Inputs to the processor 26 to calculate the $z_2$ correction can include the coordinates of the predetermined path 42, the geometry and index of refraction of the contact lens 28 and the tilt of the laser beam relative to the optical axis.

The third component, $z_3$, compensates for refraction of the laser beam caused by the anatomical configuration of the cornea 18. Specifically, it is known that the density and birefringent properties of the cornea 18 vary from location to location within the cornea 18. As the focal point 44 moves along the predetermined path 42 within the cornea 18, variations in the density and birefringent properties of the cornea 18 will affect the depth of the focal point 44 from the anterior surface 40. These variations in the density and birefringent properties of the cornea 18, however, can be compensated by $z_3$, movements. More specifically, the density of the cornea 18 can be measured and mapped using the wavefront detector 24 and the birefringent properties of the cornea 18 can be measured and mapped using an ellipsometer 22. These maps can then be input into the processor 26 to calculate $z_3$ movements that will compensate for these variations in corneal properties. Typical values for a $z_3$ correction will be in the range of 5–8 μm.

The above description provides systems and methods for moving the laser focal point 44 along the predetermined path 42. When photoablation along an interface between layers of lamellae is desired, these systems and methods can be augmented with the systems and methods of co-pending U.S. patent application Ser. No. 09/783,665, filed on Feb. 14, 2001 by Bille and entitled "A Method for Separating Lamellae" and co-pending U.S. patent application Ser. No. 09/997,167, filed on Nov. 28, 2001 by Bille and entitled "A Method for Creating a Corneal Flap". More specifically, co-pending application Ser. Nos. 09/783,665 and 09/997, 167 provide feedback type systems and methods for making minor adjustments to the depth of the laser focal point 44 to maintain the laser focal point 44 on the interface between layers of lamellae.

In another embodiment of the present invention, a contact lens 28 having a non-uniform index of refraction is used to compensate for effects on focal point depth from refraction from the contact lens 28 and variations in corneal properties. Accordingly, for this embodiment, the $z_2$ and $z_3$ movements of the laser source 12 can be reduced or eliminated. The non-uniform index of refraction can be accomplished by ion implantation of the plastic lens using masking techniques that are known in the pertinent art.

To compensate for effects on focal point depth from refraction that occurs at the posterior surface 30 and anterior surface 32 of the contact lens 28, a contact lens 28 having an index of refraction profile is used. Since this refraction is characteristic of the shape of the contact lens 28, the index of refraction profile will be the same for all lenses having the same shape. Specifically, for this embodiment, the portion of the contact lens 28 that is on the optical axis 16 will have the highest index of refraction while the periphery of the contact lens 28 will have an index of refraction that is reduced by about 3 percent.

To compensate for effects on focal point depth due to the anatomical configuration of the cornea 18, a corneal mapping of the density and birefringent properties of the cornea 18 is first prepared as described above. With the mapping, a contact lens 28 can be selectively altered via ion implantation to compensate for the variations in corneal properties. Thus, the required contact lens 28 will differ from patient to patient. However, it is contemplated that all corneas can be classified into about twenty anatomically similar groups. Thus, only about twenty different contact lenses are required to compensate for the anatomical configuration of the cornea 18 with reasonable accuracy. Selectively altering the refractive properties of the contact lens 28 has the advantage of reducing the requirements on fine adjustments of z-position of laser source 12 and provides pre-surgical quality control of the depth-profile of the desired intrastromal cut. In addition, the anterior surface of the contact lens 28 can be spherically shaped which can easily be manufactured via replica techniques and ball-shaped templates. All individual characteristics can be implemented via masking techniques in microlithographic technology.

While the particular Cornea Contact System for Laser Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, said contact lens being engageable with the cornea to conform the anterior surface thereof with said posterior surface of said contact lens;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens, the location of said laser source, and a mapping of the density of the cornea, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

2. A system as recited in claim 1 further comprising a suction ring, with said contact lens mounted to said suction ring, said suction ring for holding said contact lens against the cornea.

3. A system as recited in claim 1 wherein said input data includes an angle of tilt of the laser beam relative to the optical axis for at least one laser source location, said laser source location being distanced from said optical axis.

4. A system as recited in claim 1 wherein said contact lens has a substantially uniform index of refraction and said input data includes said index of refraction of said contact lens.

5. A system as recited in claim 1 wherein said system further comprises a wavefront analyzer for measuring corneal density at a plurality of locations within the cornea.

6. A system as recited in claim 1 wherein said radius of curvature, R, of said posterior surface of said contact lens is in a range of between approximately 7.5 mm and approximately 9.0 mm.

7. A system as recited in claim 1 wherein said predetermined path extends along a curved surface that is substantially parallel to said posterior surface of said contact lens.

8. A method for moving the focal point of a laser beam along a predetermined path within the cornea of an eye, wherein the cornea has an anterior surface and the eye defines an optical axis, said method comprising the steps of:

providing a contact lens formed with an anterior surface and a posterior surface with said posterior surface having a radius of curvature, R;

engaging said contact lens with the cornea to conform the anterior surface thereof with said posterior surface of said contact lens;

activating a laser source to generate the laser beam, direct the laser beam through said contact lens, and focus the laser beam to a focal point at a predetermined depth within the cornea;

calculating laser source movements perpendicular and parallel to said optical axis from input data including the position of said laser source, the geometry of said contact lens required to maintain the depth of the focal point from the anterior surface of the cornea as said focal point advances along the predetermined path, and an angle of tilt of the laser beam relative to the optical axis for at least one laser source location, said laser source location being distanced from said optical axis; and using said calculated laser source movements parallel to said optical axis to move the laser source relative to said contact lens and move the focal point of the laser beam along the predetermined path.

9. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, said contact lens being engageable with the cornea to conform the anterior surface thereof with said posterior surface of said contact lens;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens, the location of said laser source and a mapping of the birefringent properties of the cornea, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

10. A system as recited in claim 9 wherein said system further comprises an ellipsometer for measuring the birefringent properties of the cornea at a plurality of locations within the cornea.

11. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, and wherein said anterior surface of the contact lens is distanced from said posterior surface thereof by a distance of approximately 0.2 mm, said contact lens being engageable with the cornea to conform the anterior surface thereof with said posterior surface of said contact lens;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens and the location of said laser source, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

12. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, said contact lens being engageable with the cornea to conform the anterior surface thereof with said posterior surface of said contact lens, wherein said contact lens has a center portion and extends from the center portion to a periphery, and wherein said contact lens has an index of refraction profile with the highest index of refraction being at said center portion, $\eta_{CENTER\ PORTION}$, and said periphery having an index of refraction of approximately $0.97\eta_{CENTER\ PORTION}$;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens and the location of said laser source, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

13. A system as recited in claim 12 wherein said index of refraction profile is accomplished by ion implantation with selective masking.

14. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, said contact lens being engageable with the cornea to conform the anterior surface thereof with said posterior surface of said contact lens, and wherein said contact lens has a non-uniform index of refraction, said index of refraction being selectively varied within said contact lens to compensate for variations in corneal density within the cornea;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens and the location of said laser source, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

15. A system for moving the focal point of a laser beam along a predetermined path within the cornea of an eye, wherein the cornea has an anterior surface and the eye defines an optical axis, said system comprising:

a contact lens formed with an anterior surface and a posterior surface with said posterior surface having a radius of curvature, R, said contact lens being engageable with the cornea to conform the anterior surface thereof with said posterior surface of said contact lens, and wherein said contact lens has a non-uniform index of refraction, said index of refraction being selectively varied within said contact lens to compensate for variations in birefringence within the cornea;

a laser source for generating the laser beam, said laser source being oriented to direct the laser beam through said contact lens and having a means for focusing the laser beam to a focal point at a predetermined depth within the cornea;

a processor for receiving input data including the geometry of said contact lens and the location of said laser source, said processor operating on said input data to calculate laser source movements perpendicular and parallel to said optical axis required to maintain the depth of the focal point from the anterior surface of the cornea as said focal point advances along the predetermined path; and means responsive to said processor for moving the laser source relative to said contact lens to move the focal point of the laser beam along the predetermined path.

16. A method for moving the focal point of a laser beam along a predetermined path within the cornea of an eye, wherein the cornea has an anterior surface and the eye defines an optical axis, said method comprising the steps of:

providing a contact lens formed with an anterior surface and a posterior surface with said posterior surface having a radius of curvature, R, wherein said contact lens has a center portion and extends from the center portion to a periphery, and wherein said contact lens has an index of refraction profile with the highest index of refraction being at said center portion, $\eta_{CENTER\ PORTION}$, and said periphery having an index of refraction of approximately $0.97\eta_{CENTER\ PORTION}$;

engaging said contact lens with the cornea to conform the anterior surface thereof with said posterior surface of said contact lens;

activating a laser source to generate the laser beam, direct the laser beam through said contact lens, and focus the laser beam to a focal point at a predetermined depth within the cornea;

calculating laser source movements perpendicular and parallel to said optical axis from input data including the position of said laser source and the geometry of said contact lens required to maintain the depth of the focal point from the anterior surface of the cornea as said focal point advances along the predetermined path; and using said calculated laser source movements parallel to said optical axis to move the laser source relative to said contact lens and move the focal point of the laser beam along the predetermined path.

\* \* \* \* \*

UNITED STATES PATENT AND TRADEMARK OFFICE
CERTIFICATE OF CORRECTION

PATENT NO.    : 6,730,074 B2
DATED         : May 4, 2004
INVENTOR(S)   : Josef Bille, Klaus Baumeister and Frieder Loesel It is certified that error appears in the above-identified patent and that said Letters Patent is hereby corrected as shown below:

Column 5,
Line 8, delete "1/mm" insert -- 1°/mm --
Line 49, delete "z," insert -- $z_1$ --

Column 10,
Line 14, delete "z," insert -- $z_1$ --

Signed and Sealed this

First Day of February, 2005

JON W. DUDAS
*Director of the United States Patent and Trademark Office*